(12) United States Patent
Grasdepot et al.

(10) Patent No.: US 6,420,695 B1
(45) Date of Patent: Jul. 16, 2002

(54) METHOD FOR WAVELENGTH CALIBRATION OF AN ELECTROMAGNETIC RADIATION FILTERING DEVICE

(75) Inventors: François Grasdepot, Fontenay aux Roses (FR); Didier Dominguez, Oslo (NO)

(73) Assignee: Schlumberger Industries, S.A. (FR)

(*) Notice: Subject to any disclaimer, the term of this patent is extended or adjusted under 35 U.S.C. 154(b) by 0 days.

(21) Appl. No.: 09/623,832
(22) PCT Filed: Mar. 19, 1999
(86) PCT No.: PCT/FR99/00658
§ 371 (c)(1), (2), (4) Date: Sep. 8, 2000
(87) PCT Pub. No.: WO99/49298
PCT Pub. Date: Sep. 30, 1999

(30) Foreign Application Priority Data

Mar. 24, 1998 (FR) .............................. 98 03716

(51) Int. Cl.$^7$ .................................................. G01J 3/50
(52) U.S. Cl. ................ 250/226; 250/559.1; 250/339.13
(58) Field of Search .......................... 250/227.23, 226, 250/338.5, 339.07, 339.12, 339.13, 343, 559.1; 356/437, 436, 438

(56) References Cited

U.S. PATENT DOCUMENTS 4,140,905 A * 2/1979 Polanyi ...................... 250/281
5,451,787 A * 9/1995 Taylor ...................... 250/338.5

* cited by examiner

Primary Examiner—Que T. Le
(74) Attorney, Agent, or Firm—Straub & Pokotylo; Michael P. Straub

(57) ABSTRACT

The invention concerns a method for wavelength calibration of an electromagnetic radiation filtering device (16) included in an apparatus (10; 32) measuring spectral transmission of a propagating medium external to said apparatus and wherein said radiation flows through, said filtering device having spectral transmission tuneable on a wavelength range based on the value of a physical parameter. The invention is characterized in that it consists in: selecting at least one absorbing gaseous line which is always present in natural form in the propagation medium and whereof the corresponding wavelength is included in said filtering device tunability wavelength range; and in calibrating the filtering device with respect to said at least one absorbing gaseous line which is used as natural reference.

19 Claims, 3 Drawing Sheets

METHOD FOR WAVELENGTH CALIBRATION OF AN ELECTROMAGNETIC RADIATION FILTERING DEVICE

FIELD OF THE INVENTION

The invention concerns a method for wavelength calibration of an electromagnetic radiation filtering device included in an apparatus measuring spectral transmission of a propagating medium external to said apparatus and wherein said radiation flows through.

BACKGROUND OF THE INVENTION

Known' apparatuses such as gas analyzers, apparatuses for measurement of the calorific value of a gas or for example gas sensors comprises:

- at least one source of radiation,
- a filtering device which shows spectral transmission tunable on a wavelength range of said radiation based on the value of a physical parameter,
- a device for detection of radiation emitted by the source, the radiation source and said detection device being separated by said propagating medium.

One characteristic of a tunable filtering device is the relation between the value V of the physical parameter applied to said device and the central wavelength $\lambda_{max}$ corresponding to the transmittance maximum of the filtering device.

The relation $\lambda_{max}$ (V) can, for example, be determined using a Fourier transformation spectrometer by measuring the transmittance of the filtering device at different values V of the physical parameter applied to said device and then identifying the corresponding central wavelength values for which transmittance of the filtering device is at a maximum.

FIG. 1 represents the wavelength spectral transmission T of a filtering device tuned on several central wavelengths obtained for values V1, V2 of the physical parameter.

The wavelength calibration process is generally carried out in the laboratory and calibration therefore depends on the internal features of the spectrometer.

The apparatus is then installed on-site.

It has been noted that, during use of the apparatus, and therefore of the filtering device, the relation $\lambda_{max}$ (V) between the central wavelength for which transmittance of the filtering device is at a maximum and the control value V of the filtering device can change.

Such a change can be explained, for example, by the fact that during its use, the filtering device is subject to a temperature that is different from the temperature conditions present during calibration.

Such a change can also result from aging of the material (s) which the filtering device is made from.

Should this be the case, all that can be done is to remove the apparatus from its location and carry out another calibration of the filtering device in the laboratory, as described above, then to re-install the apparatus on-site with the re-calibrated filtering device.

It would therefore be beneficial to find a wavelength calibration method that would resolve at least one of the following two problems: carrying out calibration in the laboratory without having to use a Fourier transformation spectrometer or carrying out the calibration without having to remove the apparatus from its location.

SUMMARY OF THE INVENTION

To this end, this invention proposes a wavelength calibration method for an electromagnetic radiation filtering device included in an apparatus measuring the spectral transmission of a propagation medium external to said apparatus and wherein said radiation flows through, said filtering device having spectral transmission tunable on a wavelength range of said radiation based on the value of a physical parameter, said method comprises the steps of:

selecting at least one absorbing gaseous line which is always present in natural form in the propagation medium and whose corresponding wavelength is included in said filtering device tunability wavelength range, and in calibrating the filtering device with respect to said at least one absorbing gaseous line which is used as a natural reference.

This method is particularly easy to apply since it does not require modification of the apparatus in which the filtering device is included, for example by including a cell containing a reference gas.

Preferentially, said at least one absorbing gaseous line has a spectral width less than or equal to that of the filtering device and is sufficiently intense not to be masked by other gaseous lines.

Such a method can therefore be advantageously used to calibrate a filtering device when the apparatus in which the device is included is installed at the site where it is used.

With this method, it is no longer necessary to transport the apparatus to a laboratory to carry out its calibration since the absorbing gaseous line used as a reference is naturally present in the propagating medium.

The propagating medium can be, for example, the atmosphere and the apparatus, a carbon monoxide sensor using the carbon dioxide rays in the atmosphere as a natural reference(s).

Preferably, the apparatus also comprises:
- at least one source of electromagnetic radiation and
- a device for detection of radiation emitted by the source, said source and said detection device being separated by the propagating medium.

It is also possible to interpose the volume of gas whose spectral transmission is to be measured between the source and detection device and for this volume of gas to contain absorbing gaseous lines that can be used as natural references in accordance with the method of the invention.

In this case, the interposed volume of gas acts as the propagating medium in the sense of the invention.

If the interposed volume of gas does not occupy the entire volume between the source and detection device, it is then also possible to choose from natural gaseous lines in the gas volume and natural gaseous lines in the remaining unoccupied volume between said source and said device, those lines that are to be used.

This method can also be applied in the laboratory to calibrate the filtering device before it is used for the first time without having to use a Fourier transformation spectrometer.

More particularly, the method according to the invention consists in successively:

varying the physical parameter applied to the filtering device so that the spectral transmission maximum of said filtering device coincides with the wavelength of the reference gaseous line, deducing the coefficient(s) of the law governing the tunability of the wavelength filtering device, the general behavior of said law being known in advance, determining from this law other values of the physical parameter each corresponding to a wavelength range on which the spectral transmission of the filtering device is tuned during use.

It is possible for example to choose from said range of electromagnetic radiation wavelengths the absorbing gaseous line which has the greatest intensity with respect to the other absorbing gaseous lines.

During calibration of the filtering device, identification of this gaseous line is straightforward because it corresponds to maximum absorption in the wavelength range.

It is also advantageous to choose two absorbing gaseous lines from said range of electromagnetic radiation wavelengths rather than a single one for greater reliability of calibration.

Preferentially, electromagnetic radiation is of the infrared type.

One of the absorbing gaseous lines is, for example, that of methane at 1.666 microns.

It can also be useful to choose the absorbing line of methane at 1.791 microns, depending on the envisaged wavelength range and tunability range of the filtering device.

Preferentially, the method consists in applying an electrical field in the form of electrical voltage to the filtering device as a physical parameter but a magnetic field can also be used.

According to other characteristics:

the filtering device is a Fabry-Perot interferometer, the Fabry-Perot is a short interferometer, the Fabry-Perot interferometer is a micro-machined interferometer, the apparatus is a gas analyzer, the apparatus is an apparatus for measurement of the calorific value of a gas, the apparatus is a gas sensor.

BRIEF DESCRIPTION OF THE DRAWINGS

Other characteristics and advantages of the invention will appear from the following description, given by way of non-limiting illustrative example and made with reference to the accompanying drawings, in which.

DETAILED DESCRIPTION OF THE PREFERRED EMBODIMENTS

Figure 2:
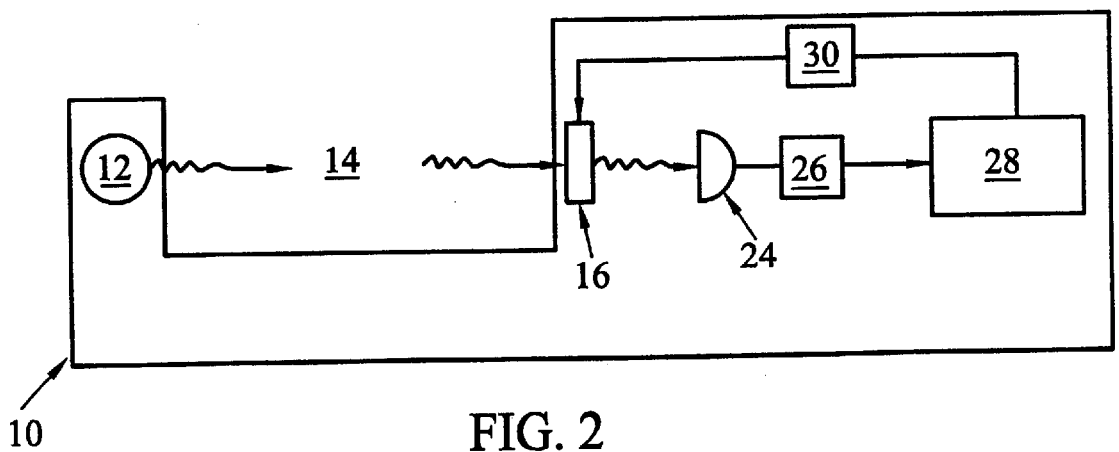
FIG. 2 represents diagrammatically of the various elements of a gas sensor.

An apparatus for determination of the concentration of a gas, such as for example a carbon monoxide sensor, is illustrated in FIG. 2 and designated by the general reference 10.

This apparatus includes a source 12 of electromagnetic radiation which is preferentially radiation situated in the infrared range. This radiation is emitted across a propagating medium 14 external to the apparatus and which is, for example, the atmosphere.

Nevertheless, radiation situated in the visible, ultraviolet, hyperfrequency or X-ray range can also be used.

The infrared radiation source 12 is, for example, a broad band-width source consisting of a tungsten filament and emits radiation of wavelengths between 0.8 to 20 $\mu$m.

The apparatus 10 comprises of a filtering device 16 which filters radiation emitted by the source 12 and which is propagated in the medium 14.

This device can also be placed directly in front of the source 12 without this altering the functioning of the apparatus.

The filtering device 16 is, for example, a short Fabry-Perot interferometer (interferometer order being 10 for example).

This filtering device can be made from silicon and manufactured using known micro-machining techniques.

For example, such a filtering device is described in documents EP 0 608 049 and EP 0 219 359 for example.

Figures 3A, 3B:
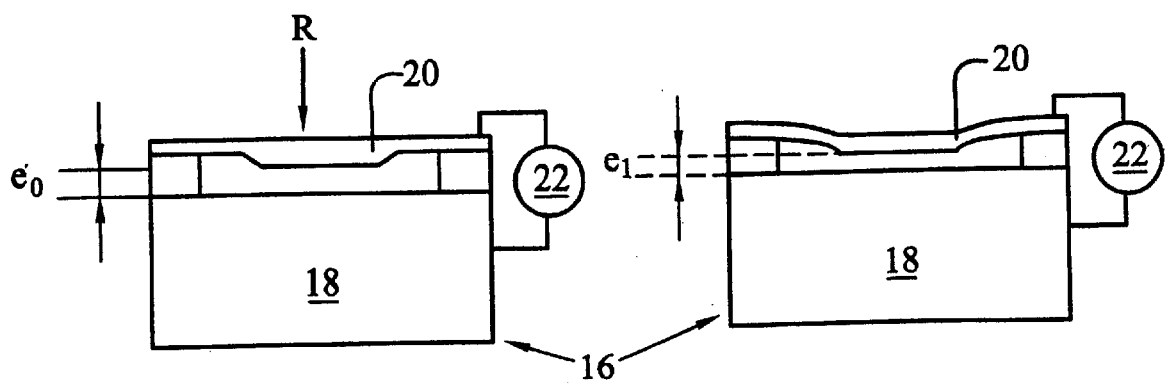
FIGS. 3a and 3b represent two successive positions of an electrically tunable filtering device for two different voltage values.

As shown in FIGS. 3a and 3b, the filtering device 16 consists of a fixed electrode 18 forming a support and a mobile electrode 20 separated from each other by a given distance $e_0$ corresponding to a position in which the mobile electrode is not deformed. In this position, called the resting position, the radiation shown by the arrow identified by the letter R in FIG. 3a is filtered for wavelength $\lambda_0$ equal to $2e_0$ (and for the harmonics of this wavelength).

Figure 1:
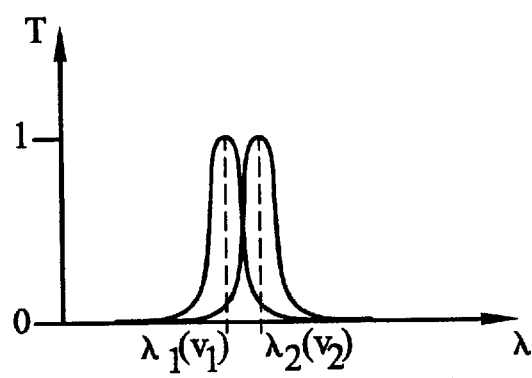
FIG. 1 has already been described.

The filtering device 16 shows spectral transmission T (represented in FIG. 1) which is tunable on a infrared radiation wavelength range as a function of the value of the physical parameter which is, for example, an electromagnetic field; in other words the transmittance maximum of the filtering device can be made to coincide with the different wavelengths included in said range by varying the electromagnetic field applied to said filtering device. More precisely, the electromagnetic field is an electrical field created by a voltage source 22.

However, it can also be a magnetic field. A magnet, for example, can be attached to a fixed electrode and a coil can be placed on a mobile electrode (or the other way round). A current circulating in the coil brings the mobile electrode closer to the fixed electrode and therefore displaces the wavelength on which the filtering device is tuned.

The physical parameter can also be temperature. In this case, the mobile and fixed electrodes can be separated by a wedge consisting of a material with a high thermal expansion coefficient which, under the effect of changes in temperature, leads to a change in the distance between the electrodes and therefore of the tunability of the filtering device on a specific wavelength. The voltage source 22 is connected to the mobile and fixed electrodes and, when voltage is applied (FIG. 3b), the mobile electrode is deformed and comes closer to the fixed electrode. The distance between the electrodes is reduced to $e_1$ ($e_1 < e_0$) and the radiation is then filtered for the wavelength $\lambda_1$ equal to $2e_1$. In this way, the filtering device is tuned on various wavelengths for different electrical voltage values.

The wavelength range is, for example, 4 to 5 $\mu$m.

The apparatus 10 also includes a detection device 24 to detect radiation which is partially absorbed in the propagating medium 14 and filtered by the filtering device 16.

The detection device 24 is a broad band-width detector such as a bolometer, thermocell or a photodiode.

The energy contained in the infrared radiation and received by the detector is transformed into an electrical signal representative of this radiation.

The signal is then amplified and converted into a numeric signal by the converter 26 then injected into the microprocessor 28.

An analogical numeric converter 30 is used to tune the spectral transmission of the filter 16 on different wavelengths.

As an initial approximation, the transmittance of an interferential filter can be regarded as gaussian $$T_f(V) = T_{max}(V) \exp - \left(\frac{\lambda - \lambda_{max}(V)}{\sigma(V)}\right)^2$$

where V is the voltage of the filter, $\lambda_{max}$ is the wavelength of the transmission maximum and $\sigma$ is its width.

For the tunable filtering device 16, the wavelength $\lambda_{max}$ of the transmission maximum varies with the control voltage V according to the formula:

$$\lambda_{max}(\lambda_{max} - \lambda_{max0}) + (KV)^2 = 0$$

where $\lambda_{max0}$ (in $\mu$m) is the wavelength of the transmission maximum of the filtering device at V=0 (=$V_0$) and K (in $\mu$m/V) is a constant dependent on the construction of the filtering device.

The filtering device is designed to be tuned between 5 $\mu$m to 4 $\mu$m with applied voltages of 0 to 20V. This corresponds to a K value approximately equal to 0.10 $\mu$m/V.

The wavelength calibration process which consists in initially establishing (that is to say before the filtering device 16 and meter 10 are used) the relation $\lambda_{max}(V)$ is carried out in the laboratory using a Fourier transformation spectrometer, as is the amplitude calibration process for the sensor. The resulting data are stored in the microprocessor 28. The filtering device is then mounted in the meter and the latter is installed at the site of use.

When the temperature to which the filtering device is subject during use differs from the temperature around said filtering device during its calibration, a wavelength shift may be produced in the filtering device which leads, for example, to the filtering device being tuned on wavelengths equal to 4.9 to 3.8 $\mu$m for voltages of 0 and 20 V respectively rather than on wavelengths of 5 and 4 $\mu$m.

If no correction is made, the gas sensor loses its accuracy in determining carbon monoxide concentration.

The invention provides for the use of at least one absorbing line of a gaseous substance present naturally in the gas volume to be analyzed in order to carry out frequency calibration of the filtering device 16 in situ.

The method according to the invention consists in choosing from the wavelength range of 4 to 5 $\mu$m a specific wavelength corresponding to an absorbing gaseous line which is always present in this range.

An absorbing line, such as that of an interfering gas, which could well disappear in the course of time or following to changes of different parameters such as temperature or pressure, should not be chosen.

In the present case, the choice of a carbon dioxide gaseous line is particularly judicious as the position of $CO_2$ gaseous lines is not dependent on either pressure or temperature and these lines are always present in the atmosphere.

For other applications (different environment, different wavelength range . . . ), it might be useful to choose a water vapor absorbing gaseous line for atmospheric measurements or a methane absorbing gaseous line.

Figure 6:
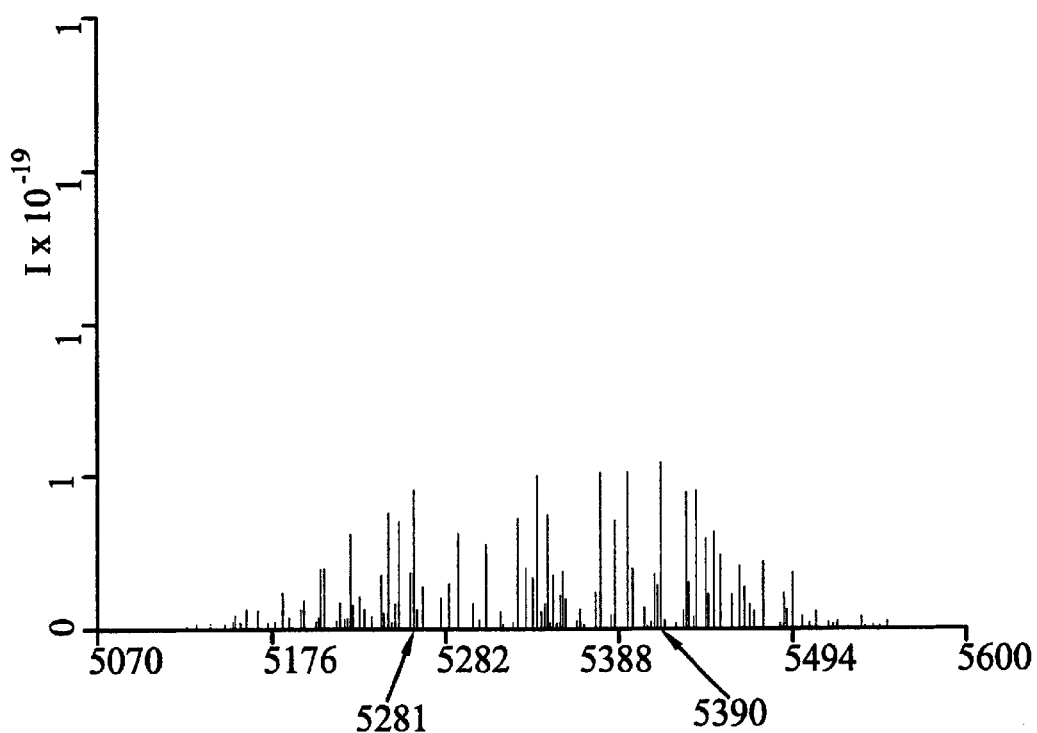
FIGS. 6 and 7 show the intensity I (in $atm^{-1} \cdot cm$) of the rotation-vibration spectra of water and carbon dioxide molecules respectively as a function of wavenumber ($cm^{-1}$).
Figure 7:
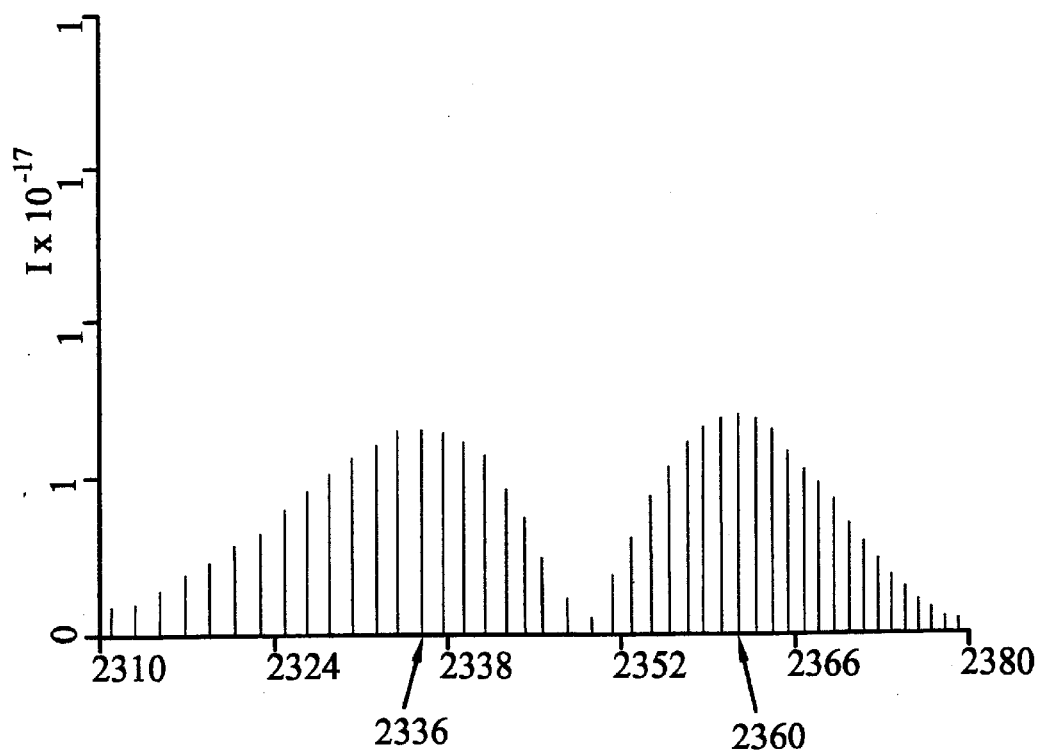

The absorbing lines of these gases are found at many wavelengths: 1.893 $\mu$m (wavenumber of about 5281 cm$^{-1}$) or 1.855 $\mu$m (wavenumber of about 5390 cm$^{-1}$) for $H_2O$ (FIG. 6), 4.280 $\mu$m (wavenumber of about 2336 cm$^{-1}$) or 4.237 $\mu$m (wavenumber of about 2360 cm$^{-1}$) for $CO_2$ (FIG. 7).

Preferentially, the absorbing line chosen should be narrow, that is to say that its width is less than or equal to the spectral width of the filtering device in the area forming a peak around the transmission maximum so that any shifts in spectral transmission of said filtering device can be detected.

Preferably, this absorbing line should also be sufficiently intense with respect to other gaseous lines in the wavelength range to allow it to be easily distinguished from these lines. If the line chosen runs the risk of being masked by other gaseous lines, then it is of no use as a natural reference for calibration. The carbon dioxide absorbing line found at a wavelength of 4.237 $\mu$m fulfils the previously defined criteria for this application and can therefore be used as a natural reference.

The spectral width of the line chosen is close to 1 nm while that of the filtering device is about 10 nm.

Before using the filtering device, as explained earlier, the device is wavelength calibrated (the relation $\lambda(V)$) and the meter is calibrated for amplitude using a standard gas whose composition is known in order to enter voltage/wavelength couples into the microprocessor 28 voltage/wavelength couple values verifying relation [1] and which correspond to the functioning points of the filtering device during use.

These couples should include the couple $V_i/4.237$ $\mu$m corresponding to the functioning point of the filtering device when spectral transmission of the device is tuned on a wavelength of 4.237 $\mu$m under an electrical voltage equal to $V_i$.

It is also possible to memorize only this couple $V_i/4.237$ $\mu$m during calibration, and to calculate and memorize at a later time other voltage/wavelength couples, corresponding to functioning points of the filtering device during its use.

After using the sensor 10 containing the filtering device, either after a predetermined length of time or for a specific reason, the filtering device might need to undergo wavelength re-calibration. To do this, a series of voltages are applied to the filtering device 16 by means of the microprocessor 28. This leads to the spectral transmission of the filtering device becoming tuned on different wavelengths [4; 5 $\mu$m]. The corresponding signal is collected for each voltage at the outlet of the detector 24.

Knowing the initial voltage $V_i$ for which spectral transmission of the filtering device was tuned on 4.237 $\mu$m, the microprocessor 28 identifies the weakest signal among the numerical signals for a filtering device position corresponding to a voltage close to $V_i$.

The voltage value $V_f$ for which this signal is obtained, is memorized along with the wavelength of 4.327 $\mu$m and the filtering device shift is given by the difference $$\Delta V = |V_f - V_i|$$

Knowing this shift and knowing the wavelength $\lambda_{max}$ on which the spectral transmission of the filtering device is to be tuned, new voltage values V' for which this tunability can be obtained are deduced from V'=V+$\Delta$V.

This method is advantageous because it allows the relation $\lambda_{max}(V)$ of the filtering device to be re-calibrated for at least one point or its wavelength stability to be verified without having to dismantle the filtering device 16 or the meter 10.

Re-calibration at several points allows to take into account more complicated $\lambda(V)$ relations than those described above.

Moreover, this method is independent of temperature and pressure since the reference line is not sensitive to these parameters.

Figure 4:
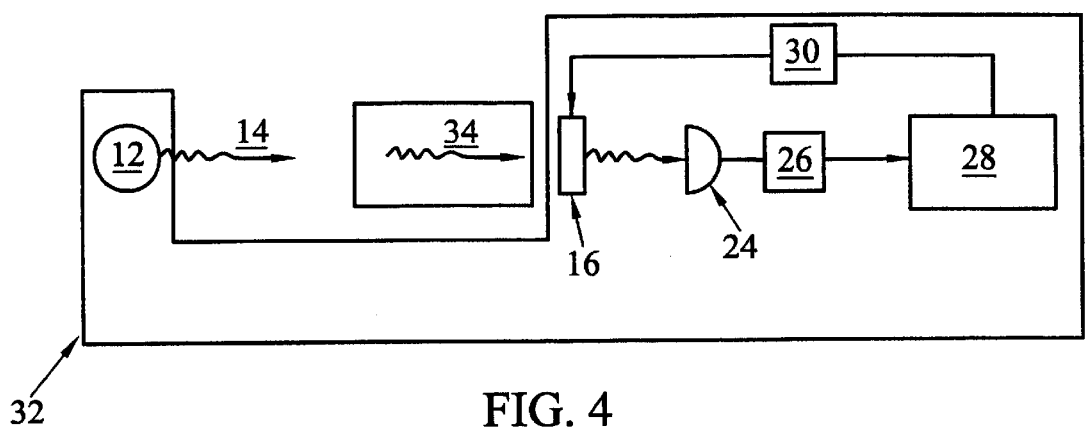
FIG. 4 is a diagrammatic representation of the various elements constituting a gas sensor in an application that is different from that of the sensor represented in FIG. 2.

In another application illustrated by apparatus 32 in FIG. 4, the apparatus of FIG. 2 retains the same structure as the previously described structure but a cell 34 containing a sample of the gas to be analyzed is placed in the propagating medium 14 along the path of the infrared radiation emitted by the source 12.

Elements identical to those in FIG. 2 are given the same references.

It is possible to either retain the absorbing gaseous line(s) which occurs naturally in the propagating medium as a reference(s) (example: $CO_2$ lines or water vapor lines), in which case the filtering device 16 calibration method as described above is applied in the same way, or to choose one or more absorbing gaseous lines present naturally in the gas in the cell whose spectral transmission is to be measured and use this for wavelength calibration of the filtering device 16.

The latter solution can for example consist in choosing methane lines in a cell containing a natural gas whose calorific value is to be measured.

According to one variant, the method according to the invention can consist in choosing two absorbing gaseous lines whose wavelengths are situated in the wavelength range in question [4; 5 $\mu$m] which are narrow, intense and always present in this range.

For example, the two lines could be those of $CO_2$ at 4.237 and 4.280 $\mu$m.

It is advantageous to choose a second absorbing gaseous line and to use this to calibrate the filtering device in view of the fact that the material(s) constituting said filtering device can age with time. The material modulus of elasticity (Young's modulus) can therefore vary and lead to changes in the previously defined constant K.

By using two absorbing gaseous line, the 2 parameters $\lambda_{max0}$ and K characterizing relation [1] can be determined as follows:

The voltages $V_1$ and $V_2$ corresponding to the first and second transmittance minimum of the filtering device 16 are investigated. In fact, this consists in investigating the local minimum around each voltage value for which the filtering device was initially tuned on the reference line wavelength.

The following values can be calculated from the values $V_1$ and $V_2$ thus obtained:

$$\lambda_{max0} = \frac{\lambda_1^2 V_2^2 - \lambda_2^2 V_1^2}{\lambda_1 V_2^2 - \lambda_2 V_1^2} \quad \text{and}$$

$$K = \frac{\sqrt{\lambda_1 \left( \frac{\lambda_1^2 V_2^2 - \lambda_2^2 V_1^2}{\lambda_1 V_2^2 - \lambda_2 V_1^2} - \lambda_1 \right)}}{V_1}$$

The voltage values to be applied to the filtering device to obtain the desired wavelengths can then be calculated from relation [1] and the coefficients $\lambda_{max0}$ and K determined above.

It should be noted that it could be useful to choose more than two absorbing gaseous lines, for example in order to improve the accuracy of re-calibration.

Investigation of these lines can be carried out by identifying the order in which they appear during the first calibration and indexing this order.

The method according to the invention can also be applied to a filtering device included in a gas-mixture analyzer or an apparatus for measuring the thermal value of a gas, for example a natural gas.

The latter is comprised of the same elements 12 and 28 as those described in FIGS. 2, 3a and 3b.

The wavelength re on which spectral transmission of the filtering device 16 can be tuned ranges, for example, from 1.50 to 1.85 $\mu$m.

Methane is a major constituent of natural gas and is always present. It is therefore particularly useful to choose the absorbing line of methane as a natural reference to carry out frequency calibration of the filtering device 16 in situ.

The line corresponding to 1.666 $\mu$m is the most intense of all the absorbing lines in the envisaged wavelength range and is sufficiently narrow ($\approx$1 nm) with respect to the spectral width of the filtering device 16 ($\approx$10 nm).

The calibration method according to the invention is applied in the same manner as described above for the CO meter.

Given that the absorbing line at 1.666 $\mu$m is the most intense of all the lines in the range [1.50; 1.85 $\mu$m], it is simple to detect the minimum signal at the outlet of the detector 24.

Figure 5:
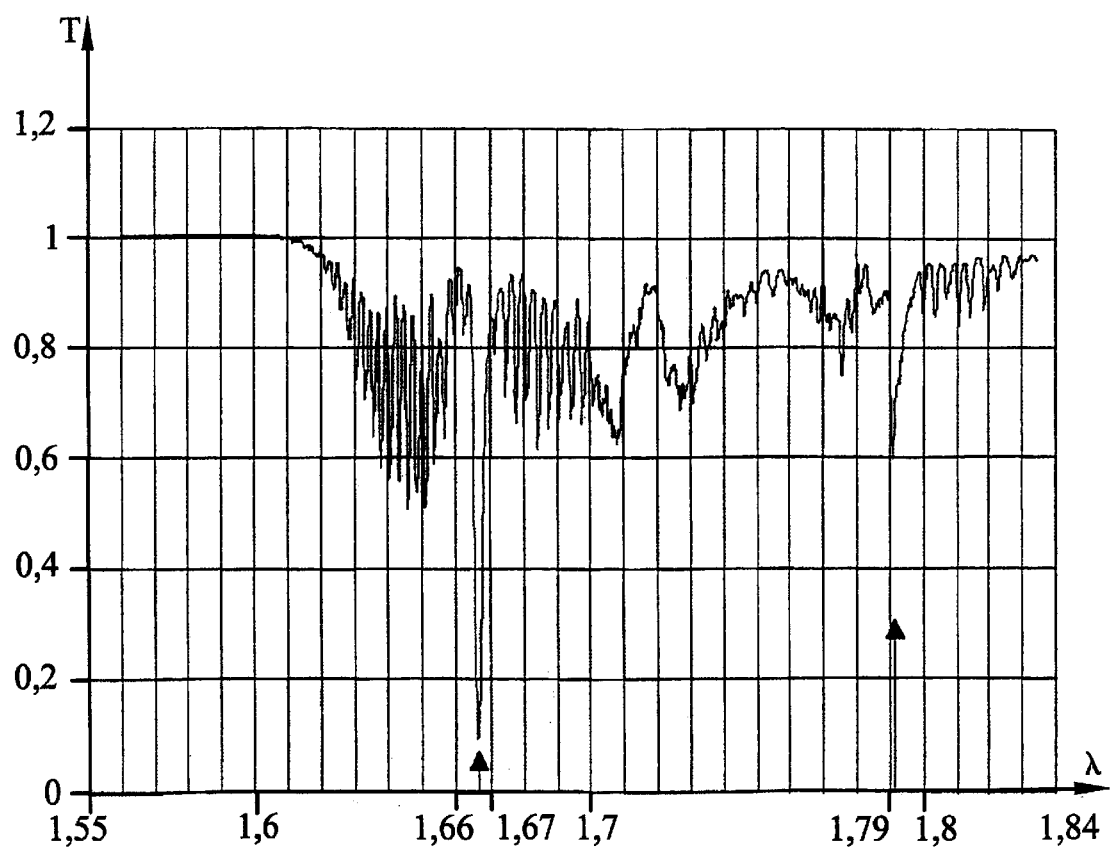
FIG. 5 shows the behavior of the methane absorbing gaseous line.

As indicated by the arrows in FIG. 5, which represent transmittance T as a function of wavelength $\lambda$, two methane absorbing lines can be chosen from the range [1.50 1.85 $\mu$m], the line at 1.666 and the line at 1.731 $\mu$m.

In this way, the previously cited advantages for the CO meter can be obtained.

For the purpose of example, the natural gas has the following composition:

| | |
|---|---|
| Methane | 89.5% |
| Ethane | 5% |
| Propane | 1% |
| Butane | 0.6% |
| Pentane | 0.3% |
| Neutral gases | 3.6% |

Several wavelengths $\lambda_1$ to $\lambda_5$ are used to determine the contribution made by the various above-cited constituents of the natural gas, with the exception of neutral gases which do not make any contribution to thermal value.

These wavelengths are such that the contribution of several combustible constituents corresponds to each one of them.

By applying a voltage V of known value, for example equal to 20V, to the filtering device 16, the filtering device tunes on a wavelength $\lambda_1$ and the detector 24 gives an electrical signal corresponding to $S_1$ (V):

$$S1(V) = \int E(\lambda) \theta \text{ gas } (\lambda, xi) \theta f(\lambda, V) Sd(\lambda) d\lambda$$

wherein E ($\lambda$) designates light intensity emitted by the source 12, $\theta$gaz ($\lambda$, $x_i$)=exp ($-L \Sigma \alpha_i(\lambda)$). xi) designates the spectral response due to all gaseous combustible constituents present at this wavelength, L designates the length of the optical path in the gas, xi represents the number of moles of combustible constituent i per unit volume at pressure P and temperature T, $\alpha_i$ designates the coefficient of absorption of the combustible constituent i and depends on wavelength, pressure and temperature, $\theta$f ($\lambda$, V) represents optical transmission due to the filtering device 16 and Sd represents the spectral response of the detector.

By tuning the filtering device 16 on different wavelengths $\lambda_1$ to $X_5$ for different voltage values $V_1$ to $V_5$, values $S_1(V_1)$ to $S_5(V_5)$ are measured. Absorbence A is defined as follows $A(V)=Ln(1/S(V))$ wherein Ln designates the Napierian logarithm, and the following five-equation system is obtained $$A_1(V_1)=a_{11}x_1+a_{21}x_2+\ldots+a_{51}x_5$$

$$A_2(V_2)=a_{12}x_1+a_{22}x_2+\ldots+a_{52}x_5$$

$$\ldots$$

$$A_5(V_5)=a_{15}x_1+a_{25}x_2+\ldots+a_{55}x_5$$

where the terms $a_{ij}$ depend on the constituent i and the apparatus 10.

Before applying the invention to a natural gas of unknown composition, a preliminary calibration step is carried out in the laboratory by injecting into apparatus 10 several gases with constituents whose number of moles per unit volume xi is known at given T and P values.

The filtering device wavelength calibration step in the laboratory is usually carried out using a Fourier transformation spectrometer.

The method according to the invention allows this calibration to be carried out without the need for a spectrometer, for example using only the methane lines at 1.666 and 1.791 μm.

To do this, a known gas mixture is injected into the apparatus 10 and the voltage V applied to the filtering device 16 is varied such that the transmission maximum of said device coincides with the wavelengths of the above-cited methane reference lines.

Once the values $V_a$ and $V_b$ are obtained, voltages for which spectral transmission of the filtering device is tuned on wavelengths 1.666 and 1.791 μm, the parameters K and $\lambda_{max0}$ (V) are determined as described above and the relation $\lambda_{max}(V)$ is then completely known.

Knowing this relation $\lambda_{max}(V)$ which is written in the form $$\lambda_{max}(V)(\lambda_{max}(V)-\lambda_{max0})+(KV)^2=0$$

as well as the wavelengths $\lambda_i$ (i=1, ... , 5), the voltages $V_i$ (i=1, ... , 5) corresponding to positions of the filtering device 16 for which the transmission maximum of said filtering device coincide with wavelengths $\lambda_i$ can be deduced.

The values K, $\lambda_{max0}$ and the couples $V_a/1.666$ μm, $V_b/1.791$ μm and $V_i/\lambda_i$ are memorized by the microprocessor 28 in FIG. 4.

The voltages $V_i$ (i=1, ... , 5) obtained in this way are successively applied to the filtering device so that its spectral transmission tunes on wavelengths $\lambda_i$ (i=1, ... , 5) and the detector provides a value $S_{i1}(V_i)$ for each couple $V_i/\lambda_1$.

In this way, a five-equation system is obtained:

$$A_{11}(V_1) = a_{11}x_1 + \ldots + a_{51}x_5$$

$$\ldots$$

$$A_{51}(V_5) = a_{15}x_1 + \ldots + a_{55}x_5$$

where $x_i$ (i=1, ... , 5) are known and the terms $a_{ij}$ are not known.

By injecting four other gas mixtures of known composition into the apparatus 10, twenty further equations are obtained with the same terms $a_{ij}$ as above.

This makes it possible to calculate by means of known mathematical methods, for example the linear equation resolution method, the coefficients $a_{ij}$ which are defined as follows:

$$[A_j]_{k=1,\ldots,5} = [a_{ij}] \; [x_i]_{k=1,\ldots,5}$$

where the indices k identify the known gas mixture in question.

It should be noted that, as a variant, it is possible to carry out a reference measurement by choosing a wavelength to which no contribution from any constituent of the gas mixture corresponds and where the corresponding voltage is deduced form the above-mentioned relation $\lambda_{max}(V)$.

This voltage is applied to the filtering device and the value $S_{ref}$ is collected at the outlet of the detector and the ratio of each of the values $S_{ij}(V_i)$ to the value $S_{ref}$ is calculated. This ratio $S_{ij}(V_i)/S_{ref}$ is then used instead of the value $S_{ij}(V_i)$ described above and allows shifts in the apparatus 10 to be avoided.

By reversing the matrix $[a_{ij}]$ using a conventional mathematical inversion method, the following system of equations is obtained:

$$[x_i]_{x=1,\ldots,5} = [a_{ij}]^{-1}_{\substack{i=1,\ldots,5 \\ j=1,\ldots,5}} [A_j]_{i=1,\ldots,5} = [b_{ij}]_{\substack{i=1,\ldots,5 \\ j=1,\ldots,5}} [A_j]_{i=1,\ldots,5}$$

In this way, the values $x_i$ are given by $$x_i = \sum_{j=1,\ldots,5} b_{ij}A_j(V),$$

All that needs to be done is to memorize the data $b_{ij}$ calculated during calibration into the microprocessor 28 memory and when a natural gas of unknown composition, and therefore of unknown calorific value, is examined, the different values Aj(V) are measured for different filter wavelengths obtained for the corresponding voltage values and the terms $x_i$ can be easily deduced from this.

The calorific value H (P,T) of the gas is given by $$\sum_{i=1,\ldots,5} x_i H_i$$

where $H_i$ represents the calorific value of constituent i in Joules per mole.

Consequently, once the terms xi are determined, the calorific value H (P,T) is obtained directly.

What is claimed is:

1. Method for wavelength calibration for an electromagnetic radiation filtering device included in an apparatus used for measuring the spectral transmission of a propagation medium external to said apparatus, said measured spectral transmission including lines corresponding to different gaseous elements of said propagation medium, and wherein said electromagnetic radiation flows through said filtering device, said filtering device having a spectral transmission having a spectral width, said spectral transmission being tunable on a wavelength range of said electromagnetic radiation based on the value of a physical parameter, said method comprising the steps of:

selecting at least one line corresponding to a gaseous element which is always present in the propagating medium, the selected line corresponding to a wavelength included in said filtering device tunability wavelength range, and calibrating the filtering device using said selected line as a reference.

2. Method according to claim 1, wherein said step of selecting at least one line includes:
   selecting a line having a spectral width less than or equal to the spectral width of the spectral transmission of the filtering device.

3. Method according to claim 1, wherein said selected line corresponds to a wavelength; and wherein said step of calibrating the filtering device includes:
   varying the physical parameter applied to the filtering device so that a spectral transmission maximum of said filtering device coincides with the wavelength corresponding to the selected line.

4. Method according to claim 1, wherein said step of calibrating the filtering device includes performing said calibrating while the filtering device is installed at its site of use.

5. Method according to claim 1, wherein the apparatus further includes at least one source of electromagnetic radiation and a device for detecting radiation, said source and said detection device being separated by said propagating medium, the method further comprising the steps of:
   operating said at least one source of electromagnetic radiation to emit electromagnetic radiation; and
   operating said device for detecting to generate said measured spectral transmission by detecting radiation including the electromagnetic radiation emitted by said at least one source.

6. Method according to claim 5, further comprising interposing a volume of gas whose spectral transmission is to be measured between the source and detection device.

7. Method according to claim 2, wherein the step of selecting at least one line includes selecting the line in the measured spectral transmission with the greatest intensity with respect to the other lines in the measured spectral transmission.

8. Method according to claim 1, wherein said step of selecting at least one line includes selecting two lines from the lines in the measured spectral transmission.

9. Method according to claim 1, wherein said electromagnetic radiation is of the infrared type.

10. Method according to claim 9, wherein the step of selecting at least one line includes selecting a line that corresponds to methane and is located in the measured spectral transmission at a location corresponding to a wavelength of 1.666 microns.

11. Method according to claim 9, wherein the step of selecting at least one line includes selecting a line that corresponds to methane and is located in the measured spectral transmission at a location corresponding to a wavelength of 1.791 microns.

12. Method according to claim 1, further comprising the step of:
   applying an electrical field in the form of electrical voltage to the filtering device as the physical parameter.

13. Method according to claim 1, wherein said filtering device is a Fabry-Perot interferometer.

14. Method according to claim 13, wherein said Fabry-Perot interferometer is a short interferometer.

15. Method according to claim 13, wherein the Fabry-Perot interferometer is a micro-machined interferometer.

16. Method according to claim 1, wherein the apparatus is a gas analyzer.

17. Method according to claim 1, wherein the apparatus is an apparatus for measurement of the calorific value of a gas.

18. Method according to claim 1, wherein the apparatus is a gas sensor.

19. Method according to claim 9, wherein the step of selecting at least one line includes selecting a line that corresponds to $CO_2$.

* * * * *